United States Patent
Saloma et al.

(10) Patent No.: US 8,227,256 B2
(45) Date of Patent: Jul. 24, 2012

(54) TWO-COLOR (TWO-PHOTON) EXCITATION WITH FOCUSED EXCITATION BEAMS AND A RAMAN SHIFTER

(76) Inventors: Caesar A. Saloma, Pasig (PH); Wilson O. Garcia, Manila (PH); Jonathan A. Palero, Quezon (PH)

( * ) Notice: Subject to any disclaimer, the term of this patent is extended or adjusted under 35 U.S.C. 154(b) by 961 days.

(21) Appl. No.: 10/529,043

(22) PCT Filed: Sep. 27, 2002

(86) PCT No.: PCT/PH02/00018
§ 371 (c)(1),
(2), (4) Date: Jan. 16, 2007

(87) PCT Pub. No.: WO2004/029690
PCT Pub. Date: Apr. 8, 2004

(65) Prior Publication Data
US 2007/0128733 A1    Jun. 7, 2007

(51) Int. Cl.
*G01N 21/64* (2006.01)
*G01N 21/62* (2006.01)
*G01N 21/63* (2006.01)
*G01J 1/52* (2006.01)
*G01J 3/443* (2006.01)

(52) U.S. Cl. ........... 436/172; 250/339.01; 250/339.06; 250/339.07; 250/353; 250/458.1; 250/459.1; 250/503.1; 250/586; 356/318; 356/319; 356/320; 356/434; 359/327; 422/82.05; 422/82.08; 422/82.11; 436/171

(58) Field of Classification Search ............ 250/339.01, 250/339.06–339.07, 353, 458.1, 459.1, 503.1, 250/586; 356/318–320, 434; 359/327, 334, 359/368; 422/82.05, 82.08, 82.11; 436/171–172
See application file for complete search history.

(56) References Cited

U.S. PATENT DOCUMENTS

| | | | |
|---|---|---|---|
| 5,034,613 A * | 7/1991 | Denk et al. | 250/458.1 |
| 5,192,980 A | 3/1993 | Dixon et al. | 356/326 |
| 5,216,483 A * | 6/1993 | Berthold et al. | 356/318 |
| 5,491,344 A * | 2/1996 | Kenny et al. | 250/461.1 |
| 5,620,571 A * | 4/1997 | Bahns et al. | 204/157.15 |
| 5,796,477 A * | 8/1998 | Teich et al. | 356/318 |
| 5,814,820 A * | 9/1998 | Dong et al. | 250/458.1 |

(Continued)

OTHER PUBLICATIONS

Bickel, G. A. et al, Journal of Chemical Physics 1987, 86, 1752-1760.*

(Continued)

*Primary Examiner* — Arlen Soderquist
(74) *Attorney, Agent, or Firm* — Ohlandt, Greeley, Ruggiero & Perle, LLP

(57) ABSTRACT

Two-color (two-photon) excitation with two confocal excitation beams is demonstrated with a Raman shifter as excitation light source. Two-color excitation fluorescence is obtained from Coumarin 6H dye sample (peak absorption=394 nm, peak fluorescence=490 nm) that is excited using the first two Stokes outputs (683 nm, 954 nm, two-color excitation=398 nm) of a Raman shifter pumped by a 6.5 nsec pulsed 532 nm-Nd:YAG laser (Repetition rate=10 Hz). The two Stokes pulses overlap for a few nanoseconds and two-color fluorescence is generateven with focusing objectives of low numerical apertures (NA≦0.4). We observed the linear dependence of the two-color fluorescence signal with the product of the average intensities of the two Stokes excitation beams. The two-color fluorescence distribution is strongly localized around the common focus of the confocal excitation beams.

7 Claims, 3 Drawing Sheets

U.S. PATENT DOCUMENTS

| | | | | |
|---|---|---|---|---|
| 5,829,448 | A * | 11/1998 | Fisher et al. | 128/898 |
| 5,887,009 | A | 3/1999 | Mandella et al. | 372/6 |
| 5,891,738 | A | 4/1999 | Soini et al. | 436/501 |
| 5,995,281 | A | 11/1999 | Simon et al. | 359/368 |
| 6,020,591 | A * | 2/2000 | Harter et al. | 250/458.1 |
| 6,094,300 | A * | 7/2000 | Kashima et al. | 359/385 |
| 6,201,989 | B1 * | 3/2001 | Whitehead et al. | 600/476 |
| 6,208,886 | B1 * | 3/2001 | Alfano et al. | 600/473 |
| 6,356,088 | B1 * | 3/2002 | Simon et al. | 324/752 |
| 6,369,928 | B1 * | 4/2002 | Mandella et al. | 359/204.1 |
| 6,414,779 | B1 * | 7/2002 | Mandella et al. | 359/212.1 |
| 6,448,088 | B1 | 9/2002 | Levine et al. | 436/164 |
| 6,667,830 | B1 * | 12/2003 | Iketaki et al. | 359/368 |
| 6,958,854 | B1 * | 10/2005 | Merriam | 359/327 |
| 2001/0045529 | A1 * | 11/2001 | Iketaki et al. | 250/493.1 |
| 2002/0109841 | A1 | 8/2002 | Gould et al. | 356/318 |
| 2002/0167724 | A1 * | 11/2002 | Iketaki et al. | 359/385 |
| 2002/0180965 | A1 * | 12/2002 | Engelhardt et al. | 356/318 |
| 2003/0013086 | A1 * | 1/2003 | Kask | 435/6 |
| 2003/0058440 | A1 * | 3/2003 | Scott et al. | 356/318 |

OTHER PUBLICATIONS

Franko, M. et al, Analytical Chemistry 1988, 60, 1925-1928.*

Hunnicutt, S. S. et al, Journal of Physical Chemistry 1989, 93, 5188-5195.*

Ueno, K. et al, Analytical Chemistry 1994, 66, 1424-1431.*

Nieuwenhuis, H. A. et al, Journal of the American Chemical Society 1995, 117, 5579-5585.*

Lakowicz, J. R. et al, Journal of Physical Chemistry 1996, 100, 19406-19411.*

Dorre K. et al, Bioimaging 1997, 5, 139-152.*

Lindek, S. et al, Optics Letters 1999, 24, 1505-1507.*

Jung, G. et al, Journal of Physical Chemistry A 2000, 104, 873-877.*

Uesugi, Y. et al, Journal of Raman Spectroscopy 2000, 31, 339-348.*

Filippidis, G. et al, Journal of Photochemistry and Photobiology B: Biology 2000, 56, 163-171.*

Cambaliza, M. O. et al, Optics Communications 2000, 184, 25-35.*

Osborne, M. A. et al, Journal of Physical Chemistry B 2001, 105, 3120-3126.*

Blanca, C. M. et al, Applied Optics 2001, 40, 2722-2729.*

Jung, G. et al, ChemPhysChem 2001, 2, 392-396.*

Xue, G. et al, Electrophoresis 2002, 23, 1490-1498.*

Lim, M. et al, Optics Communications 2002, 207, 121-130.*

Palero, J. et al, Optics Communications 2002, 211, 65-71.*

Pitcher, G. et al, "Simultaneous Two-Component Velocity and Dropsize Measurements in a Combusting Diesel Spray" in Seventh International Symposium on Applications of Laser Techniques to Fluid Mechanics, Lisbon, Portugal, Jul. 1994, 9 pages.*

Okamoto, H. et al, Journal of Raman Spectroscopy 1994, 25, 631-639.*

Wigley, G. et al, Particle & Particle System Characterization 1999, 16, 11-19.*

Dyer et al. "Laser-induced flourescence measurement of oxygen atoms above a catalytic combustor surface" Jan. 29, 1990. No. 1, pp. 111-118. Applied Optics.

Fletcher, D.G. "Two-photon excitation of atomic oxygen using a Raman-shifted ArF-excimer Laser" Jan. 1995, No. 1. pp. 61-65. Applied Physics B: Lasers and Optics.

Muraoka et al. "Diagnostics for the spatial distribution of Hydrogen atoms around the divertor Region" May 23, 1994, pp. 563-566. Journal of nuclear materials.

* cited by examiner

TWO-COLOR (TWO-PHOTON) EXCITATION WITH FOCUSED EXCITATION BEAMS AND A RAMAN SHIFTER

FIELD OF THE INVENTION

The invention relates to a method for inducing highly localized light absorption in, materials via two-color (two-photon) excitation.

BACKGROUND OF THE INVENTION

Two-color (two-photon) excitation (2CE) microscopy has been proposed [Lindek, S. and E. Stelzer, Opt Left 24 (1999), 1505-1507] where a specimen is excited by pair of photons of different wavelengths $\lambda_1$ and $\lambda_2$. The single-photon excitation (1P) wavelength $\lambda_e$ of the sample is related to $\lambda_1$ and $\lambda_2$ according to: $1/\lambda_e = 1/\lambda_1 + 1/\lambda_2$. 2CE may be implemented with two confocal excitation beams that make an angle $\theta$ with respect to each other. Two-photon excitation (2PE) is a special case of 2CF microscopy where: $\lambda_1 = \lambda_2 = 2\lambda_e = \lambda_{2p}$.

The implementation of 2CE is seriously hindered by the lack of a suitable light source that permits for an efficient two-color excitation. 2CE with $\lambda_1 = 380$ nm and $\lambda_2 = 780$ nm, has been reported earlier [Lakowicz, J., et al., J. Phys. Chem., 100 (1996), 19406-19411] with a cavity-dumped dye laser which is an excitation source that is difficult to adapt in a 2CF microscope set-up.

We have discovered a new and efficient method of achieving 2CE with two confocal excitation beams via a Raman shifter as a single light source for both $\lambda_1$ and $\lambda_2$. 2CE is demonstrated in a Coumarin 6H ($C_{15}H_{15}NO_2$) sample using the first two Stokes outputs ($\lambda_1 = 683$ nm, $\lambda_2 = 954$ nm) of the Raman shifter.

2CE with focused excitation beam(s) and a Raman shifter as light source has not yet been reported. A previous work by Uesugi et al. [J Raman Spectrosc. 31(4) (2000), 339-348] utilized two-color excitation ($\lambda_1 = 525$ nm, $\lambda_2 = 560$ nm) with a collimated beam from a Raman laser and only for excitation/absorption studies.

SUMMARY OF THE INVENTION

The present invention, in one broad sense, is the discovery that two-color (two-photon) excitation with focused beam(s) may be achieved with a Raman shifter. The process makes use of the fact that the Raman shifter could act as the light source for all the excitation wavelengths ($\lambda_1$, $\lambda_2$) that are needed in two-color excitation.

Our work provides a promising first step towards the realization of a practical 2CE microscope. The Raman shifter is a versatile excitation light source for 2CE. It is inexpensive and simpler to construct and operate than a dye laser which requires a cavity resonator, a spectrometer for spectral tuning, and a dye regulator assembly. With a Raman shifter, the optimal conditions for spatial and temporal overlap between the two excitation pulses is achieved without great difficulty unlike in set-ups where $\lambda_1$ and $\lambda_2$ are obtained from two different light sources.

Moreover, the temporal coherence of a shifter is easily controlled via the gas pressure P in the Raman cell and the Stokes (S) and anti-Stokes (aS) output frequencies are readily tuned via the pump frequency $\omega_p$ or pump energy $E_{in}$ [Garcia, W., Palero J. and C. Saloma, Opt. Commun 197/1-3 (2001), 109-114]. The Raman lines are intense, unidirectional and coherent with strongly correlated phases which most probably explains the efficiency in which 2CF has been accomplished.

BRIEF DESCRIPTION OF THE DRAWINGS

The detailed description of the invention can be readily appreciated in conjunction with the accompanying drawings, in which.

DETAILED DESCRIPTION OF THE INVENTION

The teachings of the present invention can be readily understood with reference to the accompanying figures, in which details of the preferred manner of practicing the present art are described. Accordingly, persons of skill in the appropriate arts may modify the disclosures of the present invention but still obtain the favorable results described herein. Since the underlying principles about 2CE with focused beams and a Raman shifter are key to the process, a description of the same is in order.

Figure 1:
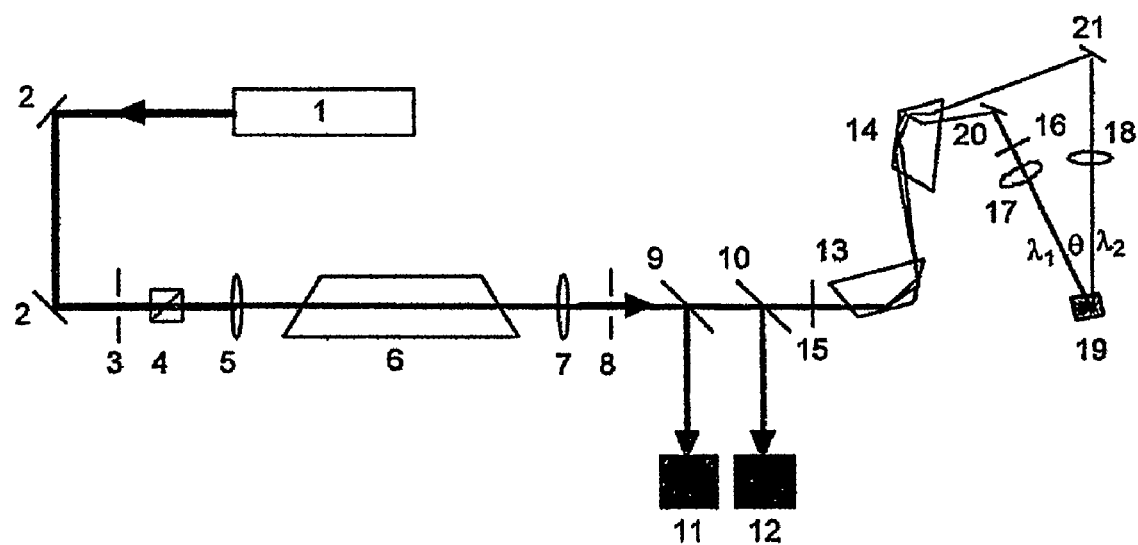
FIG. 1 is a block diagram of the set-up for 2CE with a Raman shifter that is pumped with a 10 Hz pulsed Q-switched Nd:YAG laser.

Referring to FIG. 1, a Raman shifter is optically pumped by a pulsed Q-switched Nd:YAG laser (1). The Gaussian-shaped pump pulse has a full-width at half maximum (FWHM) of 6.5 nsec. Plane mirrors (2) and lens (5) direct and focuses the pump beam into a Raman cell (6) sealed with fused Silica windows. $E_{in}$ and pump beam diameter values are adjusted via a Glan laser polarizer (4) and a diaphragm (3), respectively. The Raman outputs are collimated by a lens (7)-diaphragm (8) system and passed through a pair of dichroic mirrors (9, 10) that sequentially diverts the 532-nm line and the aS lines (<550 nm) to the beam dumps (11, 12). The continuing linearly-polarized S1 and S2 beams are then dispersed by Pellin-Broca prisms (13, 14) to obtain the two confocal excitation beams. Polarizers (15, 16) are used to vary the excitation energies of the confocal S1 and S2 beams which are focused towards the sample (19) by a pair of identical lenses (17, 18). As a demonstration, we used: $\lambda_1 = 683$ nm (S1 line) and $\lambda_2 = 954$ nm (S2 line) to obtain a value of $\lambda_e = 398$ nm, which is near the peak absorption (394 nm) of Coumarin 6H (peak fluorescence≈490 nm) in ethanol (dye concentration ~1.3 g/L). Plane mirrors (20, 21) are also used to direct the S1 and S2 beams towards the sample.

The Raman medium is 99.9999% hydrogen which has the largest Raman shift $\omega_r$ among known Raman media ($\omega_r = 4155.2$ cm$^{-1}$). The frequency of the first S-line S1 is: $\omega_{S1} = \omega_p - \omega_r$. With $\omega_p = 18,797$ cm$^{-1}$ ($\lambda_p = 532$ nm), we obtained the following Raman output lines (in nm): 192.2 (aS8), 208.8 (aS7), 228.7 (aS6), 252.7 (aS5), 282.3 (aS4), 319.9 (aS3), 368.9 (aS2), 435.7 (aS1), 683 (S1), 953.6 (S2), and 1579.5 (S3).

A Raman line is generated only if its corresponding threshold $E_{in}$ value is reached. Because the threshold values increase with the order number, the various Raman pulses are not produced simultaneously in time. In our Raman shifter, all the possible S-lines are generated when $E_{in} \geq 13.9$ mJ. The pulse energies of the S1 and S2 lines reach their peak values at $E_{in} \approx 14$ mJ, where e(S1)=23% and e(S2)=10%. At $E_{in}=14$ mJ, S3 is observed only in the P-range: $0.62 \leq P(MPa) \leq 1.03$. The aS lines are less efficient to produce [e(%)'s<10%]. Saturation prevents the e(%)'s of the Raman lines from increasing any further beyond $E_{in}=13.9$ mJ.

Before the appearance of the S2 pulse ($E_{in}<4.5$ mJ), the S1 pulse-shape (threshold=3 mJ) is approximately Gaussian with an FWHM that (slightly) decreases with $E_{in}$ (FWHM≈6 nsec at $E_{in}=2.5$ mJ). Once the S2 pulse exists (4.5 mJ<$E_{in}$<5.6 mJ), the S1 pulse-shape begins to deteriorate (and broadens) with increasing $E_{in}$. Before the S3 pulse is generated ($E_{in}<5.6$ mJ), the profile of the S2 pulse is also approximately Gaussian.

At $\theta \neq 0$, the two confocal excitation beams are separately focused by a pair of identical lenses (17, 18). We had a choice between a pair of singlets (diameter=50.8 mm, focal length=300 mm) or a pair of infinity-corrected infrared objectives (NA=0.35, working distance=6.8 mm, Nachet). Incompatibility problems between the cuvette dimensions, objective barrel design, and the 6.8 mm-working distance restricted the confocal geometry of the 0.35 NA focusing objectives to within: 100 deg<$\theta$<120 deg (or equivalently, 240 deg<$\theta$<260 deg). Confocal configuration at other $\theta$-values were realized using the singlet pair.

At the common focus, the total energy of the S1 and S2 pulses was kept at sufficiently low values (~1 mJ for $\theta=0$, and ~1.4 mJ at other $\theta$ values) to minimize the generation of unwanted 2PF signal by the individual excitation beams. It also prevents the rapid photodegradation of the dye sample. The S1 and S2 energies were made as close to each other as possible by inducing optical losses for the S1 beam as it passes through PB1, PB2, mirror M, and polarizer P2.

Figure 2:
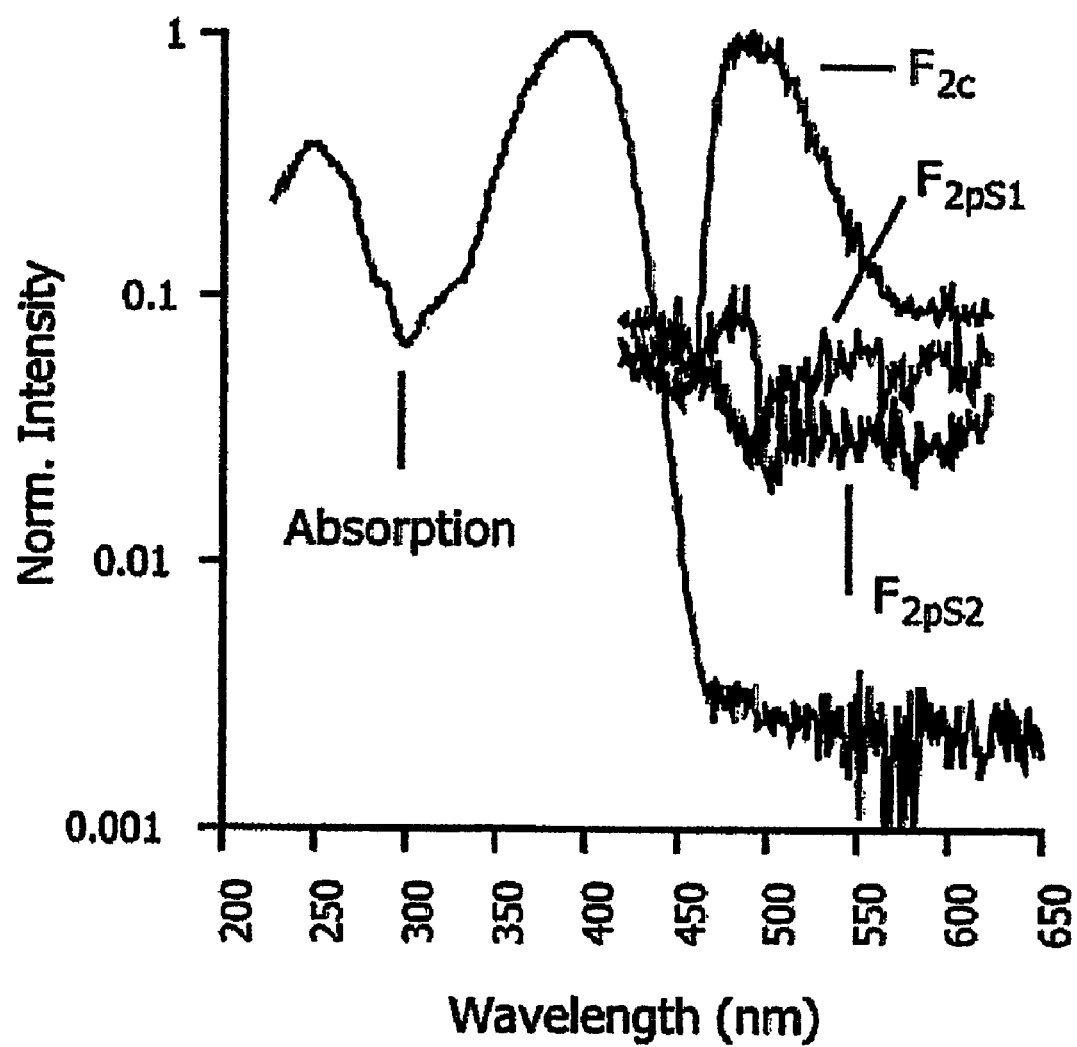
FIG. 2 shows the normalized A($\lambda$) and 2CE fluorescence signal $F_{2c}(\lambda)$ of Coumarin 6H ($E_{in} = 14$ mJ, P=0.69 MPa, $\theta = 30$ deg, NA≈0.085). $F_{2c}(\lambda)$ as compared with the residual 2PE fluorescence signals: $F_{2pS1}(\lambda)$ and $F_{2pS2}(\lambda)$, obtained with only one excitation beam present.

FIG. 2 plots (in log scale) the absorption band $A(\lambda)$ and three different types of fluorescence signals [labeled $F_{2c}(\lambda)$ $F_{2pS1}(\lambda)$ and $F_{2pS2}(\lambda)$] that were generated from the Coumarin 6H sample. A spectrophotometer was utilized to measure $A(\lambda)$ which exhibited low absorption at $\lambda>460$ nm.

The strongest fluorescence signal $F_{2c}(\lambda)$ was only detected when the two confocal S1 and S2 beams ($\theta=30$ deg) were both present in the sample. All the fluorescence signals exhibited spatial distributions that were highly localized around the common focus of the focusing singlet pair. $F_{2pS1}(\lambda)$ and $F_{2pS2}(\lambda)$ are residual signals that were detected when the sample was excited by the S1 ($\lambda_e=342$ nm) or S2 beam ($\lambda_e=477$ nm) alone. In the range: $500 \leq \lambda(nm) \leq 550$, both the $F_{2pS1}(\lambda)$ and $F_{2pS2}(\lambda)$ are an order of magnitude weaker than $F_{2c}(\lambda)$.

We determine the dependence of $F_{2c}(490$ nm) with the product $I_1 I_2$ at different $\theta$-values. Average intensity $I_1$ is proportional to the average energy $E_1$ of the S1 pulse. A similar definition holds for $I_2$. Before their angular separation, the collinear S1 and S2 beams were passed through the polarizer (15), and the $E_1$ and $E_2$ values could be simultaneously varied by rotating the said polarizer. The ratio $E_1/E_2$ was always maintained at 1.4.

At the common focus and in the absence of the sample, we measured the total average energy ($E_1+E_2$) with a pyroelectric detector. With the sample, we then measured the generated $F_{2c}$ signal for the same set of ($E_1+E_2$) values. At $\theta=110$ degrees (FIG. 3b), the confocal S1 and S2 beams were focused using a pair of 0.35 NA objective lenses. At $\theta=0$ (FIG. 3a), only one objective lens was utilized. We plotted $F_{2c}$ as a function of $I_1 I_2$ for $\theta=0$ (FIG. 3a), and 110 deg (FIG. 5b).

For both $\theta$ values, the 2CE fluorescence $F_{2c}$ plots generally exhibit a linear dependence with $I_1 I_2$. At $\theta=0$, the $F_{2c}$ values are generally larger because the confocality condition is easier to satisfy with only one focusing lens. We emphasize that the $F_{2c}$ values presented in FIGS. 3a-b, were not obtained if the S1 and S2 beams did not overlap at their common focus. We also verified that: $F_{2c}>F_{2pS1}+F_{2pS2}$.

With a Raman shifter as the excitation light source [$\lambda_1=683$ nm (S1 line), $\lambda_2=954$ nm (S2 line)], we generated a 2CF signal from a Coumarin 6H dye sample ($\lambda_e \approx 394$ nm, peak fluorescence≈490 nm). 2CE fluorescence generation was achieved with two confocal excitation beams separated by an angle $\theta$. The 2CE fluorescence signal distribution has been found to be highly localized around the common focus of the excitation beams.

A relatively strong $F_{2c}$ signal was only observed when the confocal S1 and S2 beams were both present in the sample. The residual signal $F_{2pS1}$ ($F_{2pS2}$) was to only detected when S1 (S2) was allowed into the sample. We claim that $F_{2pS1}(\lambda)$ and $F_{2pS2}(\lambda)$ are the 2PE fluorescence signals of S1 and S2, respectively. More importantly, we assert that $F_{2c}(\lambda)$ is a 2CE fluorescence signal. The fact that: $F_{2c}(\lambda)>>F_{2pS1}(\lambda)+F_{2pS2}(\lambda)$ is a simple proof that both S1 and S2 are required for $F_{2c}(\lambda)$.

Figure 3:
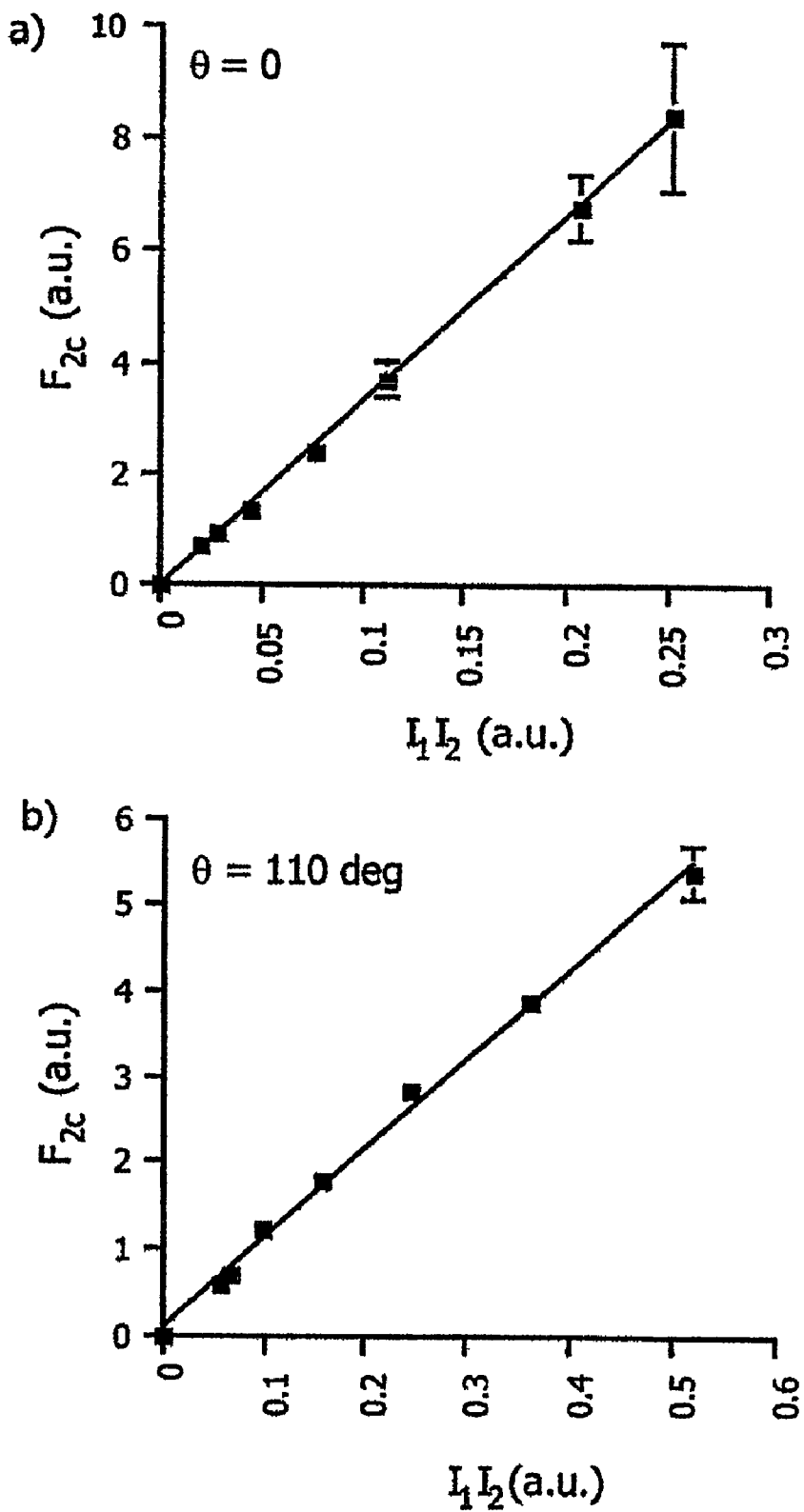
FIG. 3 presents 2CE fluorescence signal $F_{2c}$ vs. $I_1 I_2$: a) $\theta = 0$, and b) $\theta = 110$ degrees, where $E_{in} = 10$ mJ, P=0.69 MPa, NA=0.35. Values are in arbitrary units and represent the average of 10 trials.

The results in FIGS. 3a-b indicate that the theoretically predicted linear dependence of $F_{2c}$ with $I_1 I_2$ is not strictly obeyed particularly at $\theta=110$ degrees. The solid curves in FIGS. 3a-b are described by: $F_{2c}(\theta=0)=32.975 I_1 I_2 -0.004$, and $F_{2c}(110$ deg$)=10.461 I_1 I_2+0.086$, respectively. Erroneously, the curves reveal that even with $I_1$ (or $I_2$)=0, nonzero $F_{2c}$ signals are still generated. The possible causes for such errors are: (1) S1 and S2 pulses did not exactly overlapped with each other and were not totally utilized for 2CE fluorescence generation, (2) unwanted 2PE fluorescence contributions from the individual S1 and S2 beams which could be considerable when $E_1 \neq E_2$, and (3) reflective losses at the optical interfaces in the set-up which could be different for the S1 and S2 beams. At $\theta=110$ degrees, deviations from the confocality condition for the S1 and S2 beams are more likely and could result in a larger error in the measured dependence of $F_{2c}$ with $I_1 I_2$ [Lim, M. and C. Saloma, Opt. Commun. 207 (2002), 121-130].

The Raman shifter is a viable excitation light source for 2CE and we have demonstrated it in 2CE fluorescence generation. The localized nature of the 2CE fluorescence signal distribution and the versatility of the Raman shifter as an excitation light source, can still lead to interesting applications in spectroscopy. Aside from lower cost, our technique avoids the following problems which are encountered using two different excitation light sources for 2CE: (1) limitation in available excitation wavelengths which are subject to the constraint: $1/\lambda_p=(1/\lambda_S)+(1/\lambda_i)$, where $\lambda_p$, $\lambda_s$, and $\lambda_i$ are the pump, signal and idler wavelengths respectively, and (2) difficulty in achieving an optimal overlap for the two excitation pulses.

Conclusion

Two-color (two-photon) excitation has been demonstrated (in fluorescent samples) with two confocal excitation beams that were taken from the first two Stokes lines (S1 and S2) of an inexpensive hydrogen Raman shifter. 2CE fluorescence was observed only when S1 and S2 were both present in space and time. 2CF signals were detected even with low NA focusing lenses (NA<0.4) and a nonlinear dependence of the 2CF signal with the average excitation intensity was found. We emphasize that 2CE with two focused beams and a Raman shifter is not confined to fluorescence applications only. It can be applied to absorption and optical beam current generation in non-fluorescent resonant samples and semiconductor materials, respectively.

That which is claimed is:

1. A method for optical excitation of a sample via a two color (two-photon) absorption process comprising:
   (a) exciting the sample with a first wavelength of light and a second wavelength of light;
   (b) generating the first wavelength of light and the second wavelength of light from a single light source subjected to a Raman shifter, wherein the single light source is a laser beam, wherein the laser beam is adjusted by a laser polarizer and a diaphragm;
   (c) collimating an output from the Raman shifter with a lens, a first dichroic mirror associated with a first beam dump, and a second dichroic mirror associated with a second beam dump;
   (d) dispersing the output from the Raman shifter though a first Pellin-Broca prism and a second Pellin-Broca prism resulting in a first confocal excitation beam having the first wavelength of light and a second confocal excitation beam having the second wavelength of light;
   (e) directing the first confocal excitation beam and the second confocal excitation beam to the sample by mirrors; and
   (f) detecting an optical property change from the sample.

2. The method as in claim 1, wherein the sample emits a light of distinctive emission characteristics selected from the group consisting of: fluorescence, phosphorescence and Raman.

3. The method as in claim 1, wherein the laser is a high-peak power pulsed laser.

4. The method as in claim 1, wherein the Raman shifter is filled with a Raman medium, and wherein the Raman medium is a gas selected from the group consisting of hydrogen, methane, and deuterium.

5. The method as in claim 1, wherein the sample has an emitted luminescence, a surface reflected light or a refractive index change that is detected using a CCD camera, a photo-multiplier tube or a photodiode.

6. The method as in claim 1, further comprising moving the sample a pre-determined distance; and repeating steps (a) to (f) a predetermined number of times thereby creating a multitude of representations of the excitation lights.

7. The method as in claim 1, wherein the first confocal excitation beam and the second confocal excitation beam are varied in excitation energy by a polarizer.

* * * * *